United States Patent
Fedewa et al.

(10) Patent No.: US 11,443,422 B2
(45) Date of Patent: Sep. 13, 2022

(54) ADVANCED ULTRASONIC DETECTION OF DIFFERENT TISSUE TYPES

(71) Applicant: THE CLEVELAND CLINIC FOUNDATION, Cleveland, OH (US)

(72) Inventors: Russell J. Fedewa, Cleveland, OH (US); David Geoffrey Vince, Cleveland, OH (US); Hesham A. Elsharkawy, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 326 days.

(21) Appl. No.: 16/754,414

(22) PCT Filed: Oct. 15, 2018

(86) PCT No.: PCT/US2018/055949
§ 371 (c)(1),
(2) Date: Apr. 8, 2020

(87) PCT Pub. No.: WO2019/075483
PCT Pub. Date: Apr. 18, 2019

(65) Prior Publication Data
US 2020/0364854 A1 Nov. 19, 2020

Related U.S. Application Data

(60) Provisional application No. 62/571,850, filed on Oct. 13, 2017.

(51) Int. Cl.
*G06K 9/00* (2022.01)
*A61B 8/00* (2006.01)
(Continued)

(52) U.S. Cl.
CPC .......... *G06T 7/0012* (2013.01); *A61B 8/0891* (2013.01); *A61B 8/14* (2013.01);
(Continued)

(58) Field of Classification Search
CPC .................................... G06K 9/00; A61B 8/00
(Continued)

(56) References Cited

U.S. PATENT DOCUMENTS 9,465,009 B2 * 10/2016 Tsuruno ................. G01N 29/46
10,687,788 B2 * 6/2020 Kang .................... A61B 8/5207
(Continued)

OTHER PUBLICATIONS

PCT International Search Report for corresponding International Application Serial No. PCT/US2018/055949, dated Mar. 18, 2019, pp. 1-20.
(Continued)

*Primary Examiner* — Seyed H Azarian
(74) *Attorney, Agent, or Firm* — Tarolli, Sundheim, Covell & Tummino LLP

(57) ABSTRACT

A system includes a processor and, a computer-readable tangible storage device storing program instructions for execution by the processor. The program instructions include instructions for receiving ultrasonic derived data comprising an ultrasound image, representing a region of interest, and radio frequency "(RF)" data associated with the ultrasound image, and instructions for analyzing the RF data to identify at least one feature associated with a region of interest, including either or both of a feature representing a two-dimensional spectrum feature and a feature based on a cepstrum determined from the RF data. The program instructions further include instructions for classifying the region of interest as one of a plurality of anatomical classes from the identified at least one feature and causing a display to display the anatomical class.

17 Claims, 8 Drawing Sheets

(51) Int. Cl.
| | |
|---|---|
| G06T 7/00 | (2017.01) |
| A61B 8/08 | (2006.01) |
| A61B 8/14 | (2006.01) |
| G01S 7/52 | (2006.01) |
| G01S 13/89 | (2006.01) |
| G06K 9/62 | (2022.01) |
| G06V 10/25 | (2022.01) |
| G06V 10/40 | (2022.01) |

(52) U.S. Cl.
CPC .............. *A61B 8/463* (2013.01); *A61B 8/469* (2013.01); *A61B 8/5223* (2013.01); *G01S 7/52036* (2013.01); *G01S 13/89* (2013.01); *G06K 9/6282* (2013.01); *G06V 10/25* (2022.01); *G06K 9/6269* (2013.01); *G06K 9/6276* (2013.01); *G06T 2207/10132* (2013.01); *G06T 2207/30101* (2013.01); *G06V 10/40* (2022.01); *G06V 2201/03* (2022.01)

(58) Field of Classification Search
USPC ........ 382/100, 103, 106, 128–133, 154–155, 382/162, 168, 173, 181, 199, 219, 224, 382/254, 276, 286, 305; 73/598; 600/437
See application file for complete search history.

(56) References Cited

U.S. PATENT DOCUMENTS

| | | | | |
|---|---|---|---|---|
| 2006/0253033 | A1 | 11/2006 | Nair et al. | |
| 2012/0190983 | A1 | 7/2012 | Sandrin et al. | |
| 2013/0269441 | A1* | 10/2013 | Doyle | G01N 29/07 73/598 |
| 2014/0163369 | A1 | 6/2014 | Nair | |
| 2019/0336107 | A1* | 11/2019 | Hope Simpson | G06T 7/0012 |
| 2020/0364854 | A1* | 11/2020 | Fedewa | G06V 10/25 |

OTHER PUBLICATIONS

Liu, Tian, et al. "Ultrasonic tissue characterization via 2-D spectrum analysis: Theory and in vitro measurements." Medical physics 34.3 (2007): 1037-1046.

Lizzi, Frederic L., et al. "Relationship of ultrasonic spectral parameters to features of tissue microstructure" IEEE transactions on ultrasonics, ferroelectrics, and frequency control 34.3 (1987): 319-329.

Sapin, Peter M., et al. "Comparison of two-and three-dimensional echocardiography with cineventriculography for measurement of left ventricular volume in patients." Journal of the American College of Cardiology 24.4 (1994) 1054-1063.

Gao, Simon S., et al. "Optical coherence tomography angiography." Investigative ophthalmology & visual science 57.9 (2016): Oct. 27-Oct. 36.

Rodrigues, Érick Oliveira, et al. "Towards the automated segmentation of epicardial and mediastinal fats: a multimanufacturer approach using intersubject registration and random forest." 2015 IEEE International Conference on Industrial Technology (ICIT). IEEE, 2015.

Gopal, Aasha S., et al. "Left ventricular volume and endocardial surface area by three-dimensional echocardiography: comparison with two-dimensional echocardiography and nuclear magnetic resonance imaging in normal subjects." Journal of the American College of Cardiology 22.1 (1993): 258-270.

Hussain, Md Akter, Alauddin Bhuiyan, and Kotagiri Ramamohanarao. "Automatic retinal minimum distance band (mdb) computation from sd-oct images." 2015 International Conference on Digital Image Computing: Techniques and Applications (DICTA). IEEE, 2015.

Cincotti, Gabriella, Giovanna Loi, and Massimo Pappalardo. "Frequency decomposition and compounding of ultrasound medical images with wavelet packets." IEEE transactions on medical imaging 20.8 (2001): 764-771.

Eid, Hala EA. "Paravertebral block: An overview." Current Anaesthesia & Critical Care 20.2 (2009): 65-70.

Rudkin, Glenda E., Sarah E. Gardiner, and Rodney D. Cooter. "Bilateral thoracic paravertebral block for abdominoplasty" Journal of clinical anesthesia 20.1 (2008): 54-56.

Kaya, Fatma Nur, et al. "Preoperative multiple-injection thoracic paravertebral blocks reduce postoperative pain and analgesic requirements after video-assisted thoracic surgery." Journal of cardiothoracic and vascular anesthesia 20.5 (2006): 639-643.

Karmakar, Manoj K., et al. "Continuous thoracic paravertebral infusion of bupivacaine for pain management in patients with multiple fractured ribs." Chest 123.2 (2003): 424-431.

Moller, Jytte F., et al. "Thoracic paravertebral block for breast cancer surgery: a randomized double-blind study." Anesthesia & Analgesia 105.6 (2007): 1848-1851.

Davies, Richard G., Paul S. Myles, and J. M. Graham. "A comparison of the analgesic efficacy and side-effects of paravertebral vs epidural blockade for thoracotomy—a systematic review and meta-analysis of randomized trials." BJA: British Journal of Anaesthesia 96.4 (2006): 418-426.

Lonnqvist, P. A., et al. "Paravertebral blockade: failure rate and complications." Anaesthesia 50.9 (1995): 813-815.

Chelly, Jacques E. "Paravertebral blocks." Anesthesiology Clinics 30.1 (2012): 75-90.

Najarian, Melissa M., et al. "Paravertebral block: An alternative to general anesthesia in breast cancer surgery/Discussion" The American Surgeon 69.3 (2003): 213.

Abrahams, Matthew S., et al. "Evidence-based medicine: ultrasound guidance for truncal blocks." Regional Anesthesia & Pain Medicine 35.Suppl 1 (2010): S36-S42.

Bhalla, Tarun, et al. "Ultrasound-guided trunk and core blocks in infants and children." Journal of anesthesia 27.1 (2013): 109-123.

Pusch, F., et al. "Single-injection paravertebral block compared to general anaesthesia in breast surgery." Acta Anaesthesiologica Scandinavica 43.7 (1999): 770-774.

Haggard, Asher, et al. "Spectral analysis of ultrasound radiofrequency backscatter for the identification of five tissue types found in and around the paravertebral space." Medical Imaging 2018: Ultrasonic Imaging and Tomography. vol. 10580. International Society for Optics and Photonics, 2018.

\* cited by examiner

ADVANCED ULTRASONIC DETECTION OF DIFFERENT TISSUE TYPES

RELATED APPLICATIONS

This application claims priority to U.S. Provisional Patent Application Ser. No. 62/571,850 ("the '850 application"), filed Oct. 13, 2017 and entitled ULTRASONIC SPECTRAL PARAMETER DETECTION OF NEUROVASCULAR BUNDLES. The entirety of the '850 application is hereby incorporated by reference.

GOVERNMENT FUNDING

This invention was made with government support under W81XWH-16-1-0608 awarded by the Department of Defense. The government has certain rights in the invention.

TECHNICAL FIELD

This disclosure relates to medical imaging and, more particularly, to ultrasonic spectral parameter detection of different tissue types, machine learning for merging input data from multiple ultrasonic sources, and use of cepstral parameters to aid in differentiating between tissue types.

BACKGROUND

Paravertebral nerve block ("PVB") is a technique involving the injection of anesthetic in a space immediately lateral to where the spinal nerves emerge from the intervertebral foramina. PVB is commonly used for treatment of acute and chronic pain and as analgesia for various surgical procedures such as thoracic and abdominal procedures. The paravertebral space is wedge-shaped and lies on either side of the vertebral column. It is defined posteriorly by the superior costotransverse ligament (one side of the wedge), anterolaterally by the pleura (the other side of the wedge), and at the base of the wedge by the vertebral body and intervertebral disk. It extends laterally, in a continuous fashion, to the intercostal space. The intercostal artery, intercostal vein, and intercostal nerve are all contained in this space, originating medially at the spine, traversing through the paravertebral space, and extending laterally between the ribs into the intercostal space. Injection of a local anesthetic to the paravertebral space can result in ipsilateral somatic block in multiple contiguous dermatomes.

PVB is commonly performed using various modes of guidance, including landmark recognition, loss of resistance, nerve stimulation, or live fluoroscopic or ultrasound image guidance. However, using landmark recognition techniques may result in less than desirable levels of analgesia. Image guidance and live visualization of the injection typically results in more appropriate levels of analgesia and fewer complications. However, fluoroscopy subjects the patient and the anesthesiologist to a radiation dose and requires the use of contrast agents, which may not be desirable.

Ultrasound imaging is non-ionizing and non-invasive and therefore may be more desirable. Moreover, due to the real-time visualization of the needle, using ultrasound guided PVB may result in improved outcomes, reduced complications, and higher success rates. However, while visualization using ultrasound can reduce the risk of some complications, the intercostal vessels and intercostal nerve are difficult to identify during the needle injection because peripheral nerves and their associated blood vessels tend to have similar acoustic impedance as the surrounding tissue. Moreover, Doppler ultrasound may fail to locate the blood vessels arising from the need for a non-normal angle of incidence which is often difficult to achieve. Thus, a user such as a physician performing a PVB may rely on physical landmarks and relative resistance from inserting a needle in order to find a correct injection location, which may not be effective or accurate. This may result in other complications.

For carotid plaque, duplex ultrasound is commonly used for determining the position and extent of plaque within the carotid arteries. Specifically, Doppler ultrasound is used as a surrogate for the degree of stenosis. Other imaging modalities can also provide this measure: computed tomography and magnetic resonance angiography. However these are both significantly more expensive and CT exposes the patient to ionizing radiation. The degree of carotid stenosis is a primary measure to determine how best to treat the patient, but it is known plaque composition is a better approach for determining the risk of future stroke and thus composition is more important for determining how best to treat the patient.

Composition of carotid plaque is not available through any imaging modality used clinically. Magnetic resonance struggles to distinguish between fibrous and hemorrhagic plaque (former is stable while the latter is unstable). CT is very good at determining the calcium burden but struggles with distinguishing between soft tissue types. VH-IVUS is available but requires an invasive procedure to place an intravascular ultrasound probe within the carotid artery.

SUMMARY

In one example, a system includes a processor and, a computer-readable tangible storage device storing program instructions for execution by the processor. The program instructions include instructions for receiving ultrasonic derived data comprising an ultrasound image, representing a region of interest, and radio frequency ("RF") data associated with the ultrasound image, and instructions for analyzing the RF data to identify at least one feature associated with a region of interest, including either or both of a feature representing a two-dimensional spectrum feature and a feature based on a cepstrum determined from the RF data. The program instructions further include instructions for classifying the region of interest as one of a plurality of anatomical classes from the identified at least one feature and causing a display to display the anatomical class.

In another example, a system for classifying a region of interest as an anatomical feature includes a processor and a non-transitory computer readable medium storing executable instructions executable by the processor. The instructions include an ultrasound interface that receives, from an associated ultrasound system, recorded echoes from the region of interest as a set of radio frequency (RF) signals and constructs an ultrasound image from the RF signals. The RF signals including a set of harmonic signals being extracted from a frequency range associated with second harmonics of the recorded echoes. A frequency transform component transforms the RF signals from a time domain representation to a frequency domain representation. A feature extractor extracts a plurality of features from the frequency domain representation, with at least one of the plurality of features representing the set of harmonic signals. A classifier assigns the region of interest to one of a plurality of classes representing anatomical features according to the extracted plurality of features.

In yet another example, a method is provided. Recorded echoes from a region of interest are received as a set of radio frequency (RF) signals. The RF signals are transformed from a time domain representation to a frequency domain representation. The frequency domain representation is adjusted for attenuation as a function of the depth of the region of interest. A plurality of features are extracted from the frequency domain representation. The region of interest is assigned to one of a plurality of classes representing anatomical feature according to the extracted plurality of features at a classifier model.

DETAILED DESCRIPTION

Figure 1:
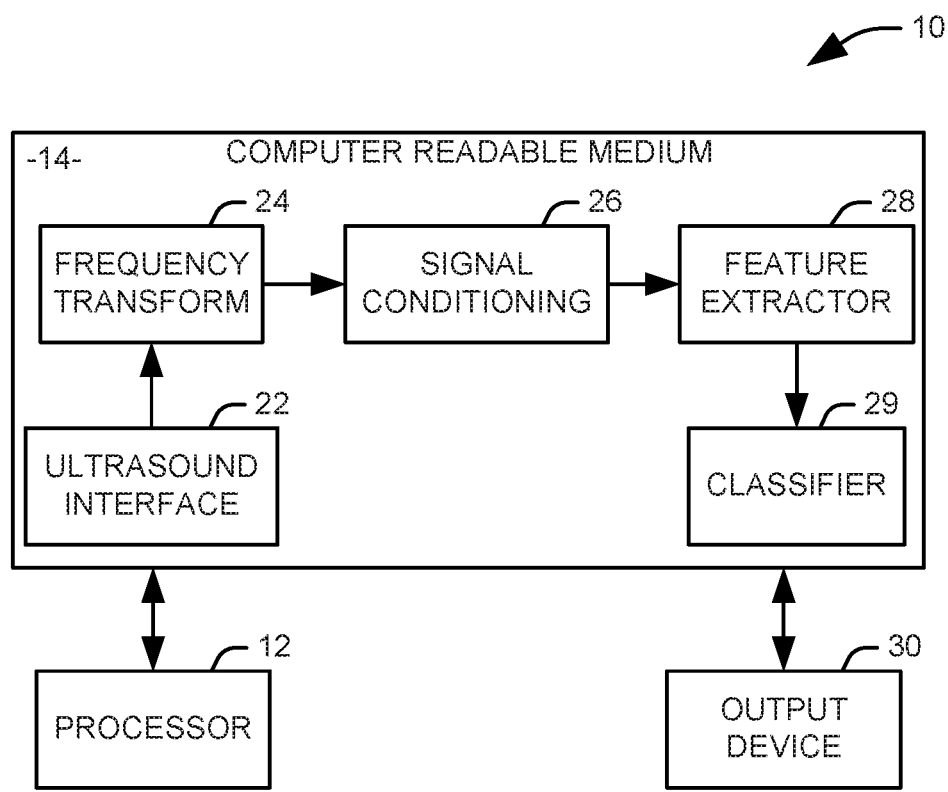
FIG. 1 illustrates a system for classifying a region of interest as one of a plurality of anatomical features.

This disclosure relates to medical imaging and, more particularly, to systems and method for identifying anatomical features within a region of interest. An anatomical feature can include any of a type of tissue, an absence of tissue (e.g., a cavity), or a known artifact caused by the presence of a certain tissue type (e.g., acoustic shadowing at the selected region of interest), or purposely caused changes in the tissue properties (e.g. changes in acoustic backscatter from heating tissue). FIG. 1 illustrates a system 10 for classifying a region of interest as one of a plurality of anatomical features. The system 10 includes a processor 12 and a non-transitory computer readable medium 14 storing executable instructions executable by the processor.

The computer readable medium includes an ultrasound interface 22 that receives, from an associated ultrasound system (not shown), recorded echoes from the region of interest as a set of radio frequency (RF) signals and constructs an ultrasound image from the RF signals. The RF signals include both signals representing a fundamental frequency associated with the ultrasound device at the time of transmitting the ultrasound from the transducer, as well as a set of harmonic signals representing a frequency range associated with nonlinearly generated second harmonic that was created during propagation or scattering of the ultrasound. In one implementation, the fundamental frequency range is between 3 and 7 MHz, with second harmonics between 5.3 and 8.7 MHz.

The inventors have determined that conditioning of the signal and extraction of appropriate classification features is simplified by converting the received signals to a frequency domain representation. Accordingly, the instructions include a frequency transform component 24 that transforms the RF signals from a time domain representation to a frequency domain representation. In one implementation, the frequency transform component 24 uses an auto-regressive spectral estimation technique to the signal to provide a power spectrum. In this example, a given region of interest can be represented as fifteen sets of sixty-four measurements. Each line can be converted separately, and then averaged, after a transformation into decibels, to provide the frequency domain representation.

The resulting frequency domain representation is then provided to a signal conditioning component 26. The signal conditioning component 26 deconvolves the frequency domain representation of the RF signals to remove a transfer function of the ultrasound system and adjusts the frequency domain representation of the RF signals for attenuation. For a homogenous propagation medium, the power spectrum $(S(f,d))$ of received signals scattered at given depth $(d)$ within the focal zone of the ultrasound system can be represented as $S(f,d)=T(f)R(f,d)D(f,d)A(f,d)B(f)$ where $f$ is the frequency, $T(f)$ and $R(f,d)$ represents the transmit and receive transfer functions of the transducer and system electronics of the ultrasound system through beam formation, $D(f,d)$ includes the effects of diffraction, $A(f,d)$ accounts for the overlying attenuation, and $B(f)$ is the backscatter transfer function.

In one implementation, an ideal reflector can be used to determine $T(f)$, $R(f, d)$, and $D(f,d)$ in a water tank. In another implementation, simulation of transmit and receive aperture beam information, as well as receive beam information (with gain stages) to obtain the spectral compensation for these items. A third implementation could use a hydrophone to determine both $T(f)$ and $D(f,d)$ while introducing a point source of ultrasound to directly measure $R(f,d)$ as a function of distance and frequency. Regardless of how estimates of $T(f)$, $R(f, d)$, and $D(f,d)$ are obtained, they can be used to compensate the frequency representation of the RF signals for these effects.

Analysis of backscattered RF data from a uniform reference phantom may also be performed to obtain an estimate of determine $T(f)$, $R(f, d)$, and $D(f,d)$ and thus compensate the received signal. The RF backscattered from the phantom is able to account for diffraction effects, transmit transfer function, and receive transfer function. It also performs a partial compensation for attenuation. The phantom needs to be a phantom with uniform scattering and acoustic properties. Ideally, this phantom should exhibit a comparable speed of sound as the tissue. For example, the CIRS model 044 phantom has a speed of sound of 1540 m/s and a uniform material with an attenuation of 0.5 dB/cm-MHz. Data is obtained from the phantom by collecting multiple frames from different regions in the phantom and then averaging the estimated power spectra across all lines and frames for the same depth as the in vivo region of interest, thus creating a reference power spectrum. Dividing the region of interest power spectrum by the reference power spectrum (or subtracting the reference power spectrum from the region of interest power spectrum if both are in decibels) removes the effects of the transmit and receive electronics and transducer, diffraction, and part of the effects of attenuation.

The signal conditioning component 26 can further provide compensation for attenuation to obtain an estimate of the backscatter transfer function (eBTF). In one implementation, a standard attenuation compensation (e.g. 0.5 dB/cm-MHz) can be used. If a reference phantom approach is used, the inherent attenuation of the phantom may suffice to obtain a useful eBTF for tissue characterization. In another implementation, attenuation compensation based on backscatter from tissue within the patent having known properties can be used. For example, in an implementation for identifying arterial plaque within an artery, adventitial tissue surrounding artery can be used. Alternatively, values for the known tissue in a normal subject or ex vivo data can be used. In either example, backscatter from the known tissue can be used to compute an estimated attenuation compensation as a function of depth for each of separate frequencies spanning the useable bandwidth. Further, the attenuation value can be adjusted based on the relative thickness of the overlying skin and fat regions as compared to the overlying muscle in the path for each patient, allowing an attenuation compensation that is adaptable to each specific patient. Finally, a spectral based approach, such as an Optimum Power-Spectral Shift Estimator (OPSSE) approach can be used.

Both the fundamental and nonlinearly-generated second harmonic portions of the backscattered data will require attenuation compensation and may require different approaches for these two types of signals. Specifically, the best attenuation compensation approach for the fundamental may likely not be the same as for the nonlinearly-generated second harmonic and vice versa, requiring the application of multiple methods for compensation.

The compensation approach to obtain an estimate of the backscatter transfer function (eBTF) using the reference phantom may be written as follows with dependence on both depth (d) and frequency (f):

$$eBTF(f) = \frac{S(f,d)}{Sref(f,d)} e^{4 a_\Delta d} \quad (2)$$

where S(f,d) is the measured signal from the carotid plaque, $S_{ref}$(f,d) is the backscattered signal from the reference phantom and $e^{4\alpha_\Delta d}$ is the attenuation coefficient to compensate for the difference between the reference phantom attenuation and the attenuation of the overlying layers of tissue between the transducer and adventitia. This compensation attenuation is determined through one of the attenuation estimation approaches listed above, and thus each of the fundamental frequencies and the harmonic frequencies can be represented by a backscatter transfer function.

A feature extractor 28 extracts at least one feature from the RF signal. In one example, at least one feature is extracted from the set of harmonic signals. Accordingly, for each of the eBTF for the fundamental frequencies and the harmonic frequencies, exemplary features can include the slope, mid-band fit, and intercept values for a regression line fit to the eBFT as a function of frequencies, an integrated backscatter over each of the upper half of the bandwidth, the lower half of the bandwidth, and the entire bandwidth, maximum and minima values in the eBTF, frequencies corresponding the maximum and minimum values, and two values extracted from a cepstrum of the eBTF, a peak cepstral value and a frequency associated with the peak cepstral value.

A classifier 29 assigns the region of interest to one of a plurality of classes representing anatomical features according to the extracted at least one feature. In one example, the classifier 29 can include one or more of a random forest model, a support vector machine, and a K nearest neighbor model. The assigned class can be stored at the non-transitory medium 20 and provided to a user at an associated output device 30, such as a display.

Figure 2:
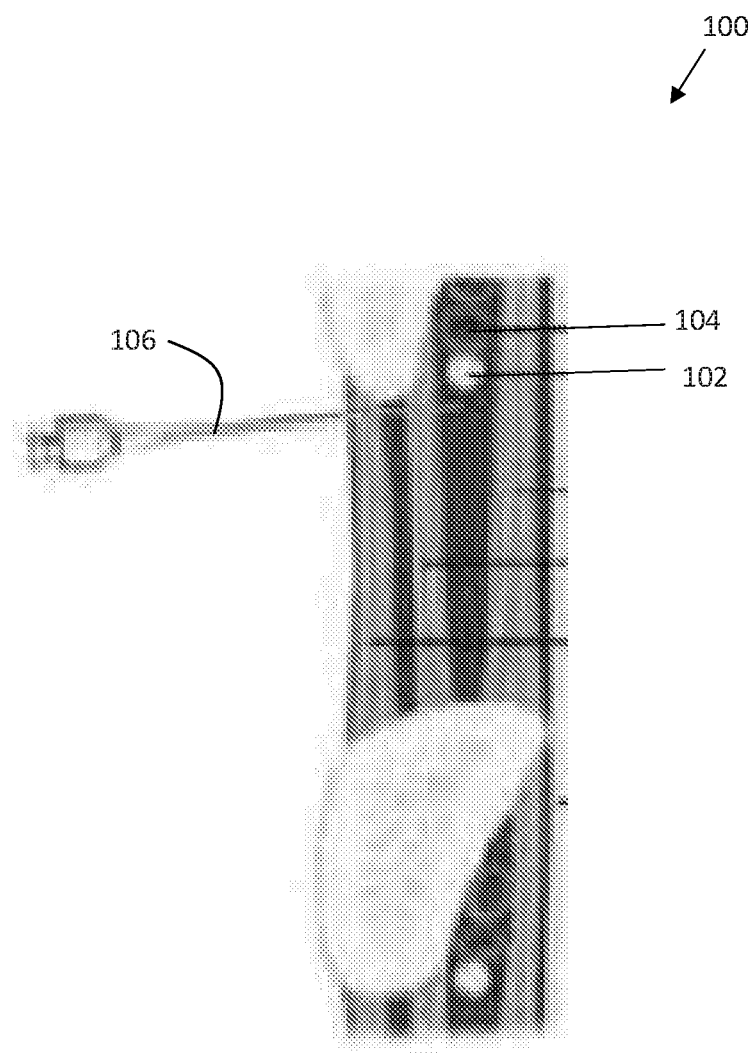
FIG. 2 illustrates an example in which the system is used in the paravertebral space.

FIG. 2 illustrates identification of nerves 102 and blood vessels 104 using a machine learning algorithm to perform spectral analysis of data obtained from ultrasound imaging of a region of interest such as a paravertebral or intercostal space 100. Identifying the nerves 102 enables visualization of the nerves while performing a medical procedure such as a paravertebral nerve block ("PVB") 106, which may result in a reduction in complications or adverse events from occurring during the procedure. In addition, identifying the blood vessels 104 enables visualization of the blood vessels 104 while performing a medical procedure, such as a PVB 106, may permit robust pain management since vessels can act as conduits for the anesthetic and reduce efficacy. This may improve patient comfort and outcomes. Although the example systems and methods described herein may refer specifically to PVB 106 procedures, the systems and methods described may similarly be used in other applications for locating nerves 102 and blood vessels 104, which may lead to the ability to minimize or avoid damage to nerve tissue and to improve outcomes. Further, it will be appreciated that the system can be used to identify other tissue and non-tissue content on the image. In one implementation, the system can differentiate between ligament tissue, intercostals muscle, other muscle tissue, pleura, shadow from the ribs or other bone, and paravertebral space, as well as nerves and blood vessels. In another implementation, it can differentiate between ablated tissue and normal tissue in the absence of microbubbles. In still another implementation, the system can differentiate between different types of arterial plaque.

Figure 3:
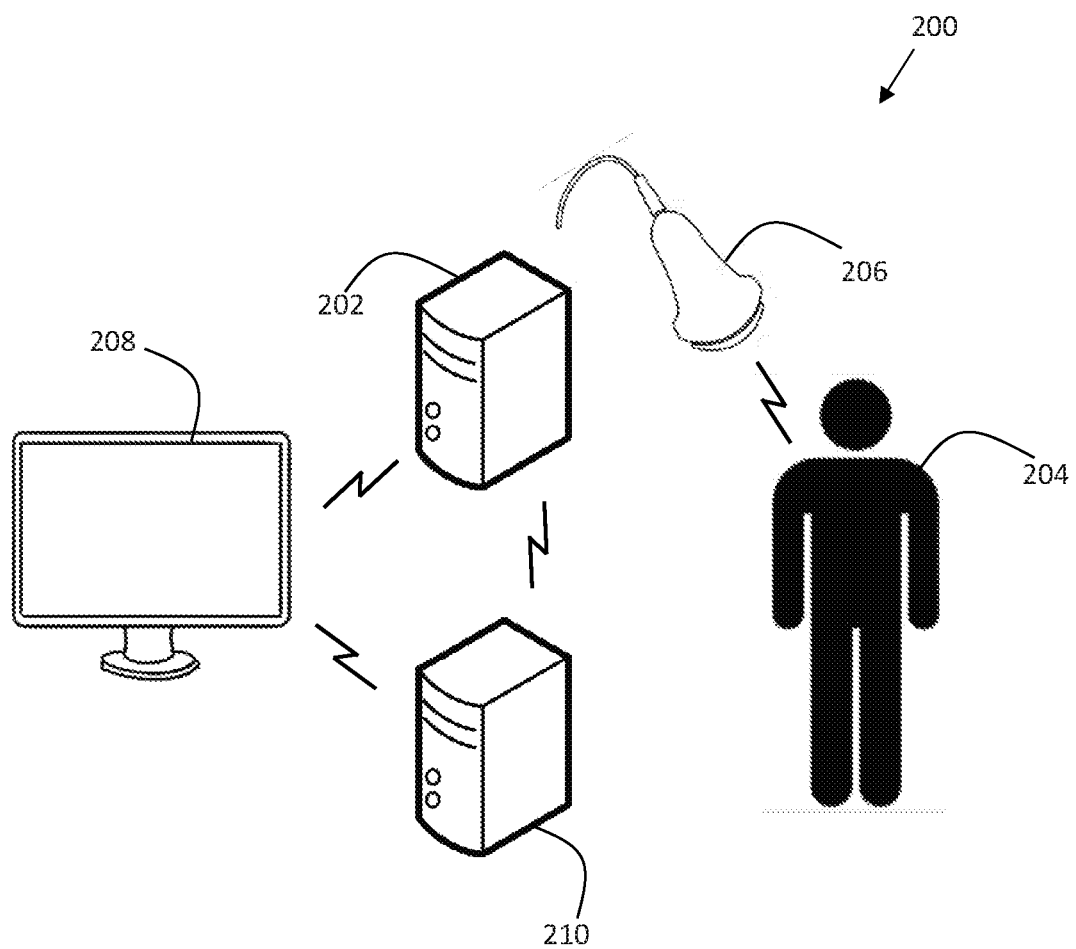
FIG. 3 illustrates an example system for identifying and classifying anatomical features.

FIG. 3 illustrates an example system for identifying and classifying tissue and other anatomical structures (hereinafter referred to as "system") 200 in a region of interest, for example, located within a paravertebral space. The system 200 includes an ultrasound computer 202 for collecting ultrasonic derived data of a patient 204 via a probe 206. The probe 206 may be directed towards any region of interest of the patient 204. In addition to capturing ultrasound images, the probe 206 also enables capturing of radio frequency ("RF") signals corresponding to the ultrasound images. In particular, the probe 206 transmits pressure waves or pulses into the tissue. Depending on the tissue density, the pulses scatter and reflect, some of which reflect and scatter back towards the probe 206. The probe 206 converts these pulses into a received electrical signal, or an RF signal.

The system 200 also includes a display 208 for displaying a display generated by the ultrasound computer 202 based on the collected ultrasonic derived data. For example, the display 208 may display ultrasound images relating to a region of interest captured by the ultrasound computer 202.

The system 200 further includes a region of interest classification computer (hereinafter referred to as "classification computer") 210. Although the classification computer 210 and the ultrasound computer 202 are illustrated as two distinct computers, the classification computer 210 and the ultrasound 202 computer may be combined into a single computing system (not shown). For example, the ultrasound computer 202 may be configured to provide the features and functionality of the classification computer 210 described herein.

The classification computer 210 is configured to receive ultrasonic derived data collected by the ultrasound computer and classify a region of interest into one of a plurality of anatomical classes. A given anatomical class can represent, for example, a type of tissue, an absence of tissue, or a known artifact caused by the presence of a certain tissue type (e.g., acoustic shadowing). In one example, the classification computer 210 is configured to receive from the ultrasound computer 202 ultrasonic derived data including acoustic radiation force impulse (hereinafter "ARFI") derived data. ARFI data may include ARFI relative stiffness data which measures the relative tissue stiffness arising from how much displacement follows the application of an ARFI push pulse. ARFI data may further include shear wave elasticity imaging (hereinafter "SWEI"), which uses an ARFI push pulse to generate shear waves propagating orthogonal to the direction of the insonifying ultrasound and ARFI data may include derivatives of the displacement measurement (e.g. velocity and acceleration). Imaging is then performed to track the shear wave propagation speed, which is directly related to Young's modulus of the tissue.

The classification computer 210 is further be configured to receive from the ultrasound computer 202 ultrasonic derived data including spectral parameters of ultrasonic backscatter which is obtained from an estimate of a backscatter transfer function ("eBTF"). The eBTF may be obtained by deconvolving the effects arising from the transmit and receive transfer functions of ultrasound computer 202, the effects of diffraction, and the effects of attenuation. The eBTF is a normalized power spectrum from which parameters are obtained from the useable bandwidth. The obtained parameters include three linear fit parameters including slope, intercept, and mid-band fit. The obtained parameters further include a root mean square ("RMS") deviation of the eBTF from the linear fit. The obtained parameters further include three integrated backscatter ("IB") parameters, or summation over defined bandwidths of the area under the eBTF, including full bandwidth, lower half of the bandwidth, and upper half of the bandwidth. The obtained parameters further include four maximum and minimum values and the corresponding frequencies over useable bandwidth of the eBTF. The obtained parameters further include two cepstral parameters, including peak value and the frequency of the peak value. A cepstrum is obtained by computing the magnitude of the Fourier transform of the power spectrum or computing the Fourier transform of the magnitude of the eBTF.

In one example, classification computer 210 receives only spectral parameters. In another example, the classification computer 210 receives both ARFI derived parameters as well as spectral parameters. The ARFI derived parameters are sensitive to the stiffness and mechanical properties of the tissues while the spectral parameters are sensitive to scatterer distribution, size, and strength of backscatter. Thus, spectral parameters and ARFI derived parameters may provide complementary information regarding tissue. Accordingly, in one example, the two ARFI data points described and the thirteen spectral parameters described are combined into a single determination of tissue type by using them as combined input to the classification computer 210. Two examples of generation and application of these parameters can be found in *Spectral Analysis of Ultrasound Radiofrequency Backscatter for the Identification of Five Tissue Types Found In and Around the Paravertebral Space*, by Haggard et al. in *Ultrasonic Imaging and Tomography*. SPIE, Vol. 10530, 1058016.

The classification computer 210 is further configured to identify and classify the region of interest based on the received ultrasonic derived data. In particular, the classification computer 210 is configured to use a supervised machine learning model to identify and classify the region of interest based on at least a portion of the received ultrasonic derived data. In one example, the classification computer 210 is configured to use at least a portion of the received ultrasonic derived data as training input in order to learn to identify and classify the region of interest. For example, the classification model can be implemented as a classification tree, a random forest method, a support vector machine, or a K nearest neighbor model.

Regardless of the supervised machine learning model implemented, the classification computer 210 is configured to learn (i.e. to be trained) based on defined standard for identifying tissue types (also referred to as a "gold standard"). In one example, the gold standard may be user interpretation of images acquired from the ultrasound computer 202. Images may be selected, for example, for use by the classification computer 210 for training based on a degree of user confidence. In another example, the gold standard reference may be based on histology or other suitable imaging modalities. Although the intercostal space provides a very limited acoustic window and thus there is often no Doppler signal from blood vessels, stiffness and scattering does not depend on the insonification angle with respect to blood flow, and therefore the data provided by the ultrasound computer 202 remains a robust measure of tissue type.

The classification computer 210 is further configured to (subsequently after being trained) perform statistical analysis on the received ultrasonic derived data in order to identify and classify the region of interest. The classification computer 210 is further configured to communicate to the display 208 the identified region of interest. For example, the classification computer 210 causes the display 208 to augment an ultrasound image provided by the ultra sound computer 202 with the identified nerve and vessel information in order to provide a user such as a physician the ability to visualize nerves and vessels while performing a medical procedure such as a PVB.

Figure 4:
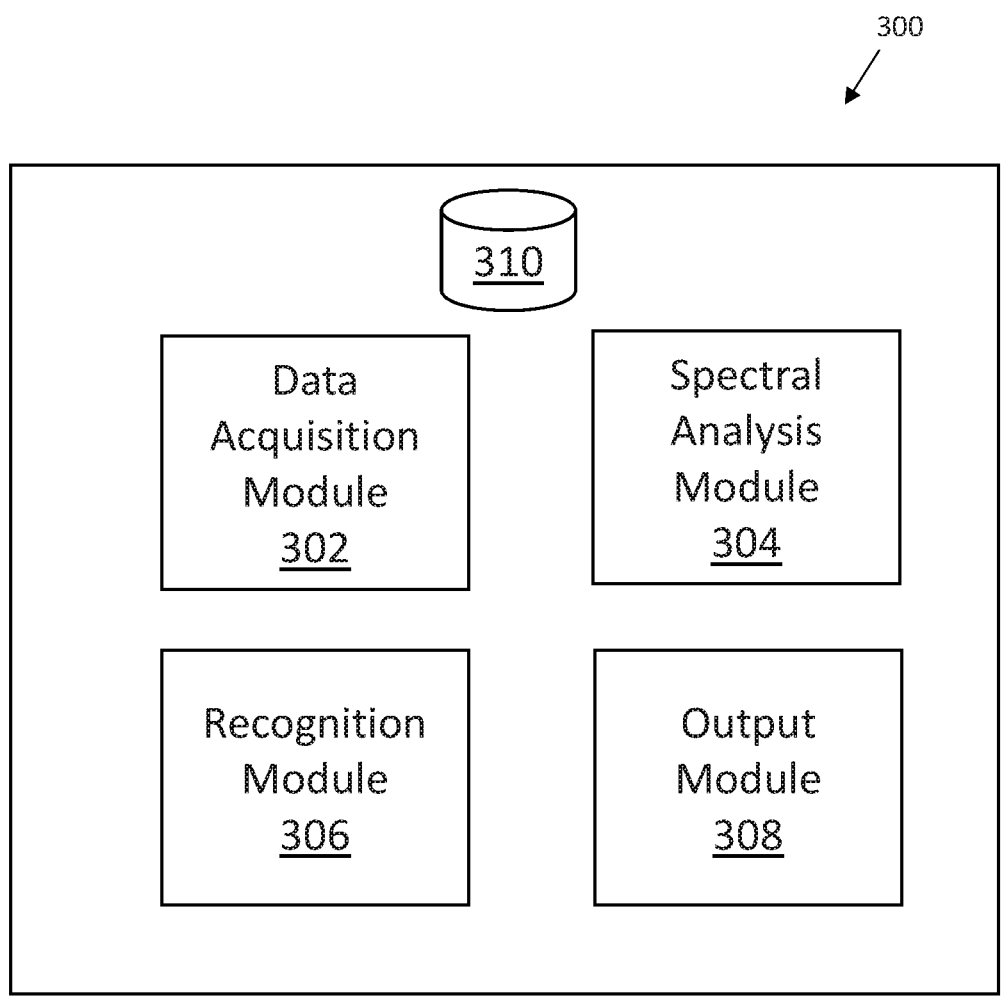
FIG. 4 illustrates a block diagram of an example classification computer used by the system in FIG. 3.

FIG. 4 illustrates a block diagram of an example classification computer 300 (e.g. the classification computer 210 of FIG. 3). The classification computer 300 includes a data acquisition module 302 for receiving ultrasonic derived data from an ultrasound computer (i.e. the ultrasound computer 202 of FIG. 3). In one example, the data acquisition module 302 stores the ultrasonic derived data in a database 310 for further processing. The ultrasonic derived data includes ultrasound images as well as underlying RF data associated with the ultrasound images. In one example, the ultrasonic derived data further includes color Doppler loops for use a reference for identification of intercostal arteries and/or veins and to aid in selection of regions of interest for analysis.

The classification computer 300 includes a spectral analysis module 304 for analyzing RF signals for selected regions of interest in order to identify features for the selected regions of interest. In one example, the spectral analysis module 304 is configured to identify or calculate three feature categories for each region of interest, including spectral features based on a frequency spectrum of one dimensional signals traversing the regions of interest, two-dimensional spectral features, and cepstrum-based features.

In one example, the spectral analysis module 304 is configured to perform spectral analysis of the RF signals using an autoregressive ("AR") model. The AR model of spectral estimation does not require zero-padding and may have better frequency resolution than alternative approaches. The AR model may also excel for short time series analysis as compared to alternative approaches. Thus, the AR model may be a desirable choice for implementation by the spectral analysis module 304. However, in other examples, the spectral analysis module 204 may implement alternative models for performing spectral analysis.

An AR model of a random process can be described by the equation:

$$x[n] = -\sum_{k=1}^{p} a[k] \times [n-k] + e[n] \quad (3)$$

where p is defined as the AR order, a[k] are valued as the AR coefficients, and e[n] is a white noise random process. The present value is modeled as a weighted sum of past values with the additive noise term e[n] that has the white noise variance $\sigma^2$.

The power spectral density (PSD) can be estimated from the AR model as shown in the following equation:

$$PSD_{AR}(f) = \frac{\sigma^2}{\left|1 + \sum_{k=1}^{p} a[k]\exp(-j2\pi fk)\right|^2} \quad (4)$$

where PSD is the power spectral density as a function of frequency (f), $\sigma^2$ is the variance of the white noise, a[k] are the AR coefficients, and p is the AR order of the model. The Yule-Walker system of equations are obtained through a relationship between the AR coefficients and the autocorrelation function that can be used to generate the AR-based PSD and leads to the following form:

$$\begin{bmatrix} R_{XX}(0) & R_{XX}(-1) & L & R_{XX}(-p) \\ R_{XX}(1) & R_{XX}(0) & L & R_{XX}(-p+1) \\ M & M & M & M \\ R_{XX}(p) & R_{XX}(p-1) & L & R_{XX}(0) \end{bmatrix} \begin{bmatrix} 1 \\ a_1 \\ M \\ a_p \end{bmatrix} = \begin{bmatrix} \sigma^2 \\ 0 \\ 0 \\ 0 \end{bmatrix} \quad (5)$$

where $\sigma^2$ is the variance of the white noise, and $R_{xx}$ is the autocorrelation calculated from the signal. These equations can be solved recursively using the Levinson-Durbin algorithm, incrementally computing the AR parameters $\{a_1, a_2, \ldots, a_p, \sigma^2\}$. The variance of the noise, $\sigma^2$, is equal to the modeling error in the spectral estimate for this model. Because of this, the AR parameters can be computed recursively, with increasing order p until reducing the error to an applicant dependent level.

Some of the noise introduced by increasing the order of the AR model may aid in the process tissue characterization when dealing with diffuse scattering of ultrasound waves from heterogeneous tissue. Therefore, an optimal range of AR order may exist, where it is large enough to create an accurate spectral estimate and include useful noise for tissue characterization, but not so large that the noise obfuscates the data. To select appropriate AR-orders to investigate, the spectral analysis module 304 is configured to observe mean squared error (MSE) using an order penalizing cost function. In one example, the spectral analysis module 304 is configured to use one of three order-penalizing cost functions, including: Final Prediction Error (FPE), Akaike's Information Criterion (AIC), and Minimum Description Length (MDL). The cost functions for each of these techniques can be defined by the given equations, respectively:

$$FPE = \frac{N+p+1}{N-p-1}\sigma(p)^2 \quad (6)$$

$$AIC = N \ln[\sigma(p)]^2 + 2p \quad (7)$$

$$MDL = N \ln[\sigma(p)]^2 + p \ln N \quad (8)$$

where p is the AR order, $\sigma(p)^2$ is the error as a function of p order, and N is the number of samples used for analysis.

The spectral analysis module 304 is further configured to use the RF signal for each A-line in a region of interest to compute a PSD (also referred to as "spectra") using the AR model. In one example, the spectral analysis module 304 is configured to compute multiple spectra for different region of interest sizes, order, and at different bandwidths. In such an example, the spectral analysis module 304 is further configured to average and normalize the spectra via spectral subtraction using acquired calibration data.

In one example, the spectral analysis module 304 is configured to generate a linear regression of amplitude on frequency from the normalized data and compute eight spectral parameters from the regression line and the normalized data, including: (1) maximum power and (2) its corresponding frequency, (3) minimum power and (4) its corresponding frequency, (5) a Y-intercept of the regression line and (6) slope of the regression line, (7) mid-band fit, and (8) an integrated backscatter parameter.

Figures 5A, 5B:
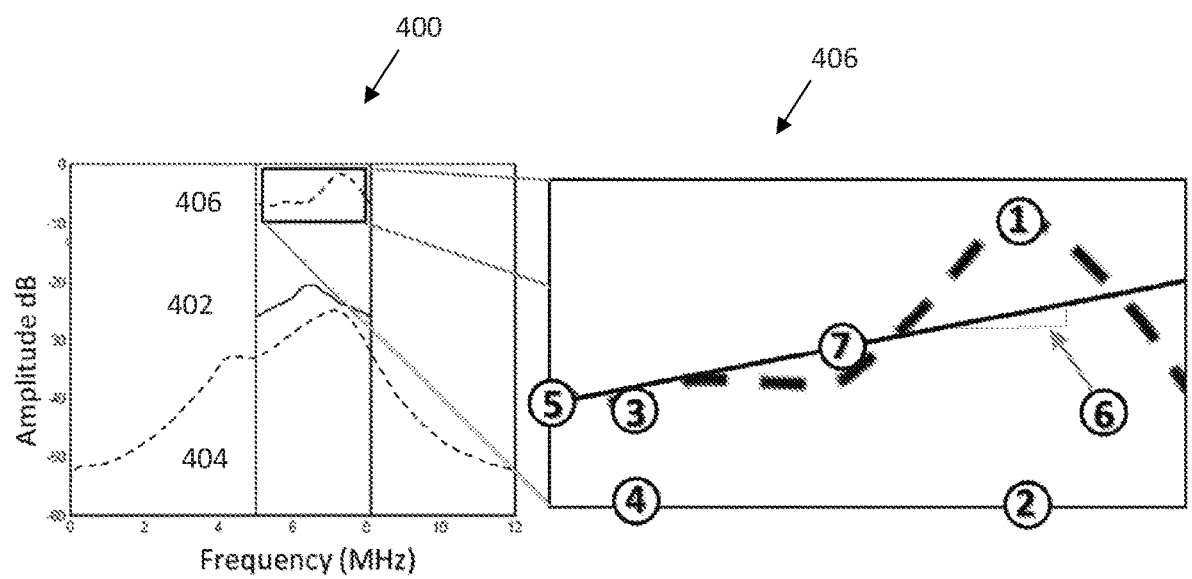
FIG. 5A is a graph illustrating an average spectrum from a single region-of-interest including a normalized spectrum.
FIG. 5B is a graph illustrating a zoomed in view of the normalized spectrum of FIG. 5A.

FIG. 5A is a graph 400 illustrating the average spectrum from a single region-of-interest is shown 402, along with the normalization spectrum from the same depth as the selected region of interest 404, and the resulting normalized spectrum 406. FIG. 5B illustrates a zoomed in view of the normalized spectrum 406 and associated regression line, including the eight spectral parameters: maximum power 1, its corresponding frequency 2, minimum power 3, its corresponding frequency 4, Y-intercept 5, slope of the regression line 6, and mid-band fit 7. Integrated backscatter is not illustrated but can be defined by the equation:

$$IBS = \frac{1}{f_{max} - f_{min}} \int_{f_{min}}^{f_{max}} S(f)df \quad (9)$$

where S(f) is the normalized power spectral density (PSD) computed by the AR-model-based method.

Referring again to FIG. 4, the one-dimensional ("1-D") parameters calculated for each ROI contain frequency content only in the range direction, parallel with the beam. Thus, in one example, to supplement the 1-D spectral information, the spectral analysis module 304 is further configured to compute and include two-dimensional ("2-D") spectral parameters in the feature set for classification. A two-dimensional spectral feature, as the term is used herein, represents frequency content in both a range direction of the ultrasound beam as well as a cross-range direction. In one example, the spectral analysis module 304 is configured to compute the 2-D spectral parameters using a Hamming window and zero padding the samples in the region of interest to 1024 in each direction. The spectral analysis module 304 is further configured to compute the Fourier transform in the range direction, to normalize the range-oriented magnitude spectra, and to compute the Fourier transform in the cross-range direction, yielding the 2-D PSD, designated as $S_{2D}(k,\mu)$.

Figure 6:
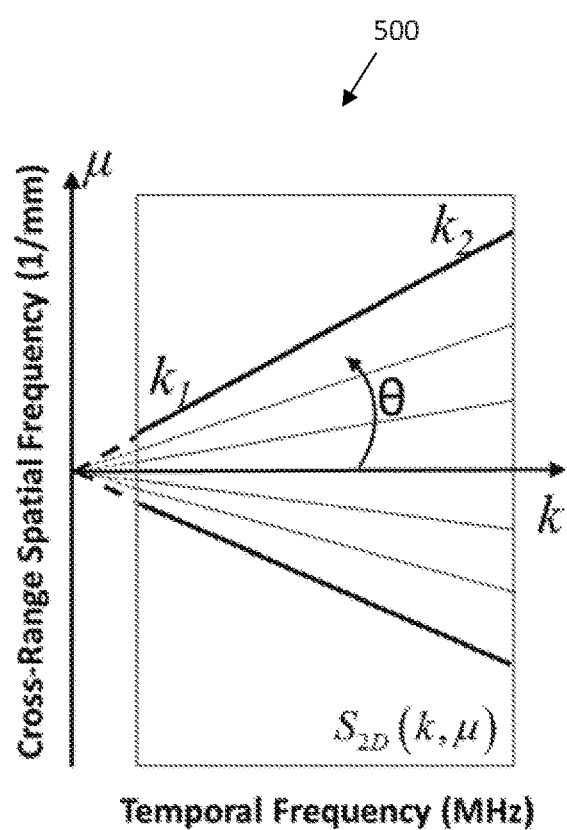
FIG. 6 is a graph illustrating example geometry for computing radially-integrated spectral power.

The geometry for computing radially-integrated spectral power (RISP) is illustrated by the graph 500 in FIG. 6. RISP is a function of angle, as illustrated by the graph 500 in FIG. 6, and can be defined in Equation:

$$RISP(\theta) = \frac{\int_{k_1}^{k_2} S'_{2D}(k, \mu) dk}{\int_{k_1}^{k_2} dk} \quad (10)$$

where the spatial frequency is effectively replaced using the definition of the radial coordinate angle $$\mu = k \tan(\theta) \quad (11)$$

and $$S_{2D}'(k,\mu) = 10 \log S_{2D}(k,\mu) \quad (12)$$

Figure 7:
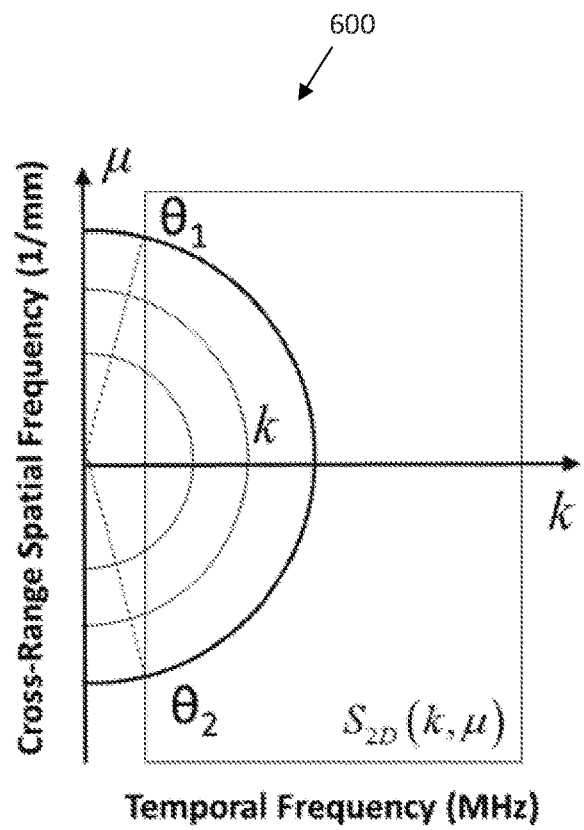
FIG. 7 is a graph illustrating angularly-integrated spectral power.

Integration is performed along radial lines over the temporal frequency range from $k_1$, the low end of the frequency band, to $k_2$, the upper end of the frequency band. Angularly-integrated spectral power (AISP) is illustrated by the graph 600 in FIG. 7. AISP is a function of radius (K) and is defined below in Equation:

$$AISP(K) = \frac{\int_{\theta_1}^{\theta_2} S'_{2D}(k, \mu) K d\theta}{\int_{\theta_1}^{\theta_2} K d\theta} \quad (13)$$

where $$K = \sqrt{k^2 + \mu^2} \quad (14)$$

and the range of the angles is constrained by the usable bandwidth. In one example, four 2-D spectral parameters are derived from the RISP and AISP functions, and included the peak value of RISP, the 3 dB bandwidth of RISP, the slope of a regression line fit to AISP, and the intercept of a regression line fit to AISP.

Referring again to FIG. 4, in one example, in addition to 1-D and 2-D spectral parameters, a feature based on the cepstrum may be included for classification. Accordingly, the spectral analysis module 304 is further configured to calculate a power cepstrum of a signal segment in a region of interest according to the Equation:

$$\text{Power Cepstrum} = |\mathcal{F}^{-1}\{\log(|\mathcal{F}\{f(t)\}|^2)\}|^2 \quad (15)$$

In particular, the power cepstrum of a signal is defined as the squared magnitude of the inverse Fourier transform of the logarithm of the squared magnitude of the Fourier transform of a signal. The spectral analysis module 304 is further configured to calculate an average cepstrum for the region of interest and to extract the peak of the average cepstrum to use in classification.

The classification computer 300 further includes a recognition module 306 for recognizing or classifying region of interest in a region of interest based on the features or spectral parameters provided by the spectral analysis module 304. In one example, the recognition module 306 classifies region of interest based on a combination of spectral parameters provided by the spectral analysis module 304 and acoustic radiation force impulse ("ARFI") derived information, as previously described.

In one implementation, the recognition module 306 can comprise one or more pattern recognition classifiers, each of which utilize the extracted features or a subset of the extracted features to determine an appropriate class. Where multiple classifiers are used, an arbitration element can be utilized to provide a coherent result from the plurality of classifiers. Each classifier is trained on a plurality of training images representing various classes of interest. The training process of the a given classifier will vary with its implementation, but the training generally involves a statistical aggregation of training data from a plurality of training images into one or more parameters associated with the output class. Any of a variety of optimization techniques can be utilized for the classification algorithm, including support vector machines, self-organized maps, fuzzy logic systems, data fusion processes, boosting and bagging methods, rule based systems, or artificial neural networks.

For example, a SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. A rule-based classifier applies a set of logical rules to the extracted features to select an output class. Generally, the rules are applied in order, with the logical result at each step influencing the analysis at later steps. In one implementation, the SVM can be implemented via a kernel method using a linear or non-linear kernel.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used.

The classification computer 300 further includes an output module 308 for communicating with a display (e.g. the display 208 of FIG. 3) and for causing changes to the display, and in particular for causing the display to display data provided by the recognition module 306. The output module 308 may be configured to communicate with the display via either a wired or wireless connection. In one example, the output module 308 is configured to overlay or merge data provided by the recognition module 306 with other data provided to the display, such as images provided to the display by an ultrasound computer (e.g. the ultrasound computer 202 of FIG. 3).

Figure 8:
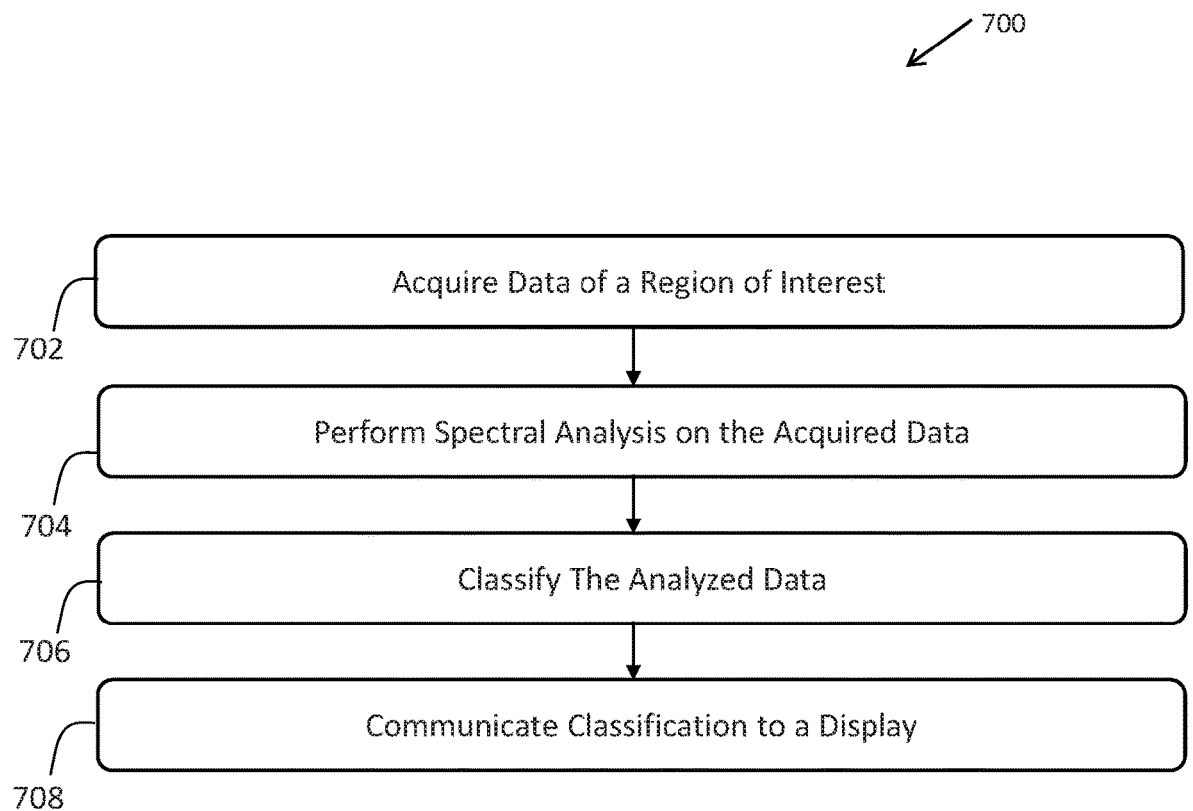
FIG. 8 illustrates an example method for identifying and classifying a region of interest in an anatomy of a patient.
Figure 9:
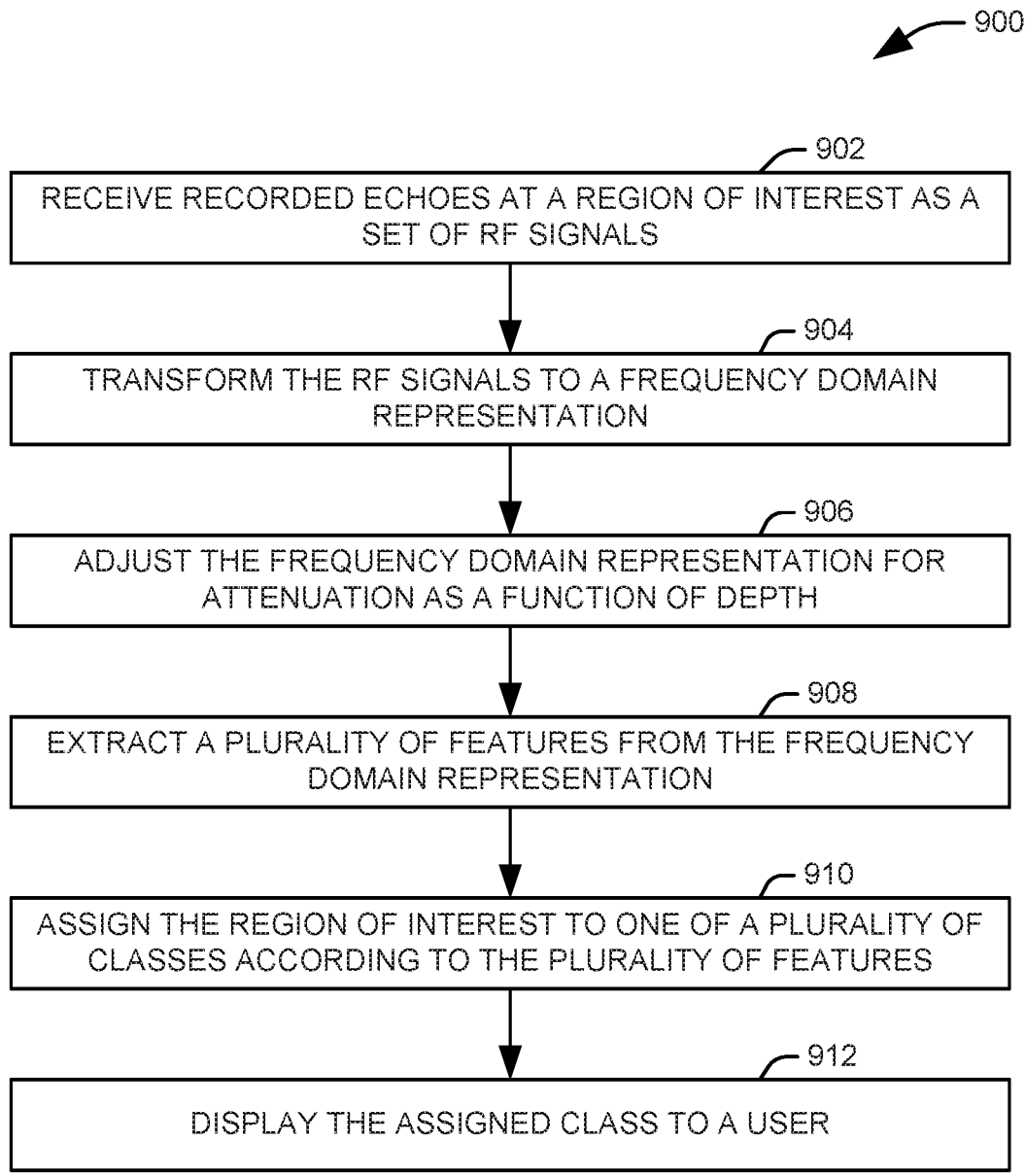
FIG. 9 illustrates a method for classifying a region of interest into one of a plurality of classes representing anatomical features.

In view of the foregoing features described above, an example method will be better appreciated with reference to FIGS. 8 and 9. While, for purposes of simplicity of explanation, the method is shown and described as executing serially, it is to be understood and appreciated that the method is not limited by the illustrated order, as parts of the method could occur in different orders and/or concurrently from that shown and described herein.

FIG. 8 illustrates a method for identifying and classifying a region of interest in an anatomy of a patient. At 702, ultrasound images, including RF and Doppler data, are acquired by an ultrasound imaging system (e.g. the ultrasound computer 202 of FIG. 3) from an anatomy of a patient. In one example, the ultrasound images are taken of a paravertebral space and an intercostal space. In one example, ultrasound images are taken on both side of an area on the anatomy. In one example, both acoustic radiation force impulse derived data and spectral parameters of ultrasonic backscatter is received. The ultrasound images are stored for further retrieval and analysis.

At 704, spectral analysis is performed by a computer (e.g. the classification computer 210 of FIG. 3) on the acquired ultrasound images to identify at least one feature associated with the region of interest. In one example, a plurality of features in three categories are identified, including one dimensional spectral features, two-dimensional spectral features, and cepstrum-based features. In one example, the spectral analysis is performed using an autoregressive ("AR") model. In one example, a plurality of spectra are computed, based on the AR model, for different region of interest sizes, order, and at different bandwidths, and the plurality of spectra are averaged and normalized via spectral subtraction using acquired calibration data. In one example, eight spectral parameters are computed from the normalized data, including: maximum power, frequency corresponding to maximum power, minimum power, frequency corresponding to maximum power, Y-intercept, slope of a regression line, mid-band fit, and integrated backscatter.

At 706, the region of interest is classified using supervised machine learning based on the at least one identified feature. In one example, one of single classification tree, random forest, support vector, and K nearest neighbor supervised machine learning is used to classify the region of interest as a particular type of tissue or anatomical feature. At 708, a display is caused to alter its output and to display the classification for the region of interest.

FIG. 9 illustrates a method 900 for classifying a region of interest into one of a plurality of classes representing anatomical features. At 902, recorded echoes from an ultrasound system are received from a region of interest as a set of radio frequency (RF) signals. In one implementation, the RF signals including a set of harmonic signals being extracted from a frequency range associated with second harmonics of the recorded echoes. At 904, the RF signals are transformed from a time domain representation to a frequency domain representation. In one example, the signals can be transformed to provide a first frequency domain representation, representing fundamental frequencies of the ultrasound device, and a second frequency domain representation, representing second harmonic frequencies of the fundamental frequencies.

At 906, the frequency domain representation is adjusted for attenuation as a function of the depth of the region of interest. In one example, this function is patient specific, such the attenuation is adjusted as a function of each of the depth of the region of interest and a ratio of a thickness of skin and fat to a thickness of muscle within the patient. In another example, the attenuation function can be determined from a subject other than a subject associated with the region of interest, using measured backscatter from known tissue. This can also be performed with a phantom or an ex vivo tissue sample. The attenuation function can also be frequency specific, such that a first function is associated with a first frequency band and a second function is associated with a second frequency band, and the frequency domain representation is adjusted for attenuation with the first function for signals within the first frequency band and with the second function for signals within the second frequency band.

At 908, a plurality of features are extracted from the frequency domain representation. In one implementation, at least one feature is extracted from a frequency domain representation of the set of harmonic signals. Alternatively or additionally, the features can include at least one of a two-dimensional spectral feature and a feature based on a cepstrum determined from the set of harmonic data. At 910, the region of interest is assigned to one of a plurality of classes representing anatomical feature according to the extracted plurality of features at a classifier model, and the assigned class is displayed to a user at 912.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system comprising:
   at least one processor; and
   at least one non-transitory computer-readable medium storage device storing program instructions for execution by the at least one processor, the program instructions comprising:
   first program instructions for receiving ultrasonic derived data comprising an ultrasound image, representing a region of interest, and radio frequency "(RF)" data associated with the ultrasound image;
   second program instructions for analyzing the RF data to identify at least one feature associated with the region of interest, the at least one feature including one of a two-dimensional spectral feature and a feature representing a cepstrum determined from the RF data;

third program instructions for classifying the region of interest as one of a plurality of anatomical classes from the identified at least one feature using a machine learning model; and fourth program instructions for causing a display to display the one of the plurality of anatomical classes;

wherein the second program instructions are configured to perform a linear regression of amplitude on frequency from the RF data to provide a regression line and calculate a plurality parameters from the normalized data, comprising: a maximum power, a frequency corresponding to the maximum power, a minimum power, a frequency corresponding to the maximum power, a Y-intercept of the regression line, a slope of the regression line, mid-band fit, and an integrated backscatter parameter.

2. The system, of claim 1, wherein the at least one feature is a two-dimensional spectral feature.

3. The system of claim 1, wherein the at least one feature represents the cepstrum.

4. The system of claim 1, wherein the RF signals including a set of harmonic signals being extracted from a frequency range associated with second harmonics of the recorded echoes, and the at least one feature includes a feature representing the set of harmonic signals.

5. The system of claim 1, wherein the plurality of anatomical classes each represent a type of arterial plaque.

6. The system of claim 1, wherein the third program instructions use, as the machine model, one of a random forest model, a support vector machine, and a K nearest neighbor model.

7. A system for classifying a region of interest as an anatomical feature comprising:
a processor; and
a non-transitory computer readable medium storing executable instructions executable by the processor comprising:
an ultrasound interface that receives, from an associated ultrasound system, recorded echoes from the region of interest as a set of radio frequency (RF) signals and constructs an ultrasound image from the RF signals, the RF signals including a set of harmonic signals being extracted from a frequency range associated with second harmonics of the recorded echoes;
a frequency transform component that transforms the RF signals from a time domain representation to a frequency domain representation;
a feature extractor that extracts a plurality of features from the frequency domain representation, at least one of the plurality of features representing the set of harmonic signals;
and
a classifier that assigns the region of interest to one of a plurality of classes representing anatomical features according to the extracted plurality of features;
wherein the second program instructions are configured to perform a linear regression of amplitude on frequency from the RF data to provide a regression line and calculate a plurality parameters from the normalized data, comprising: a maximum power, a frequency corresponding to the maximum power, a minimum power, a frequency corresponding to the maximum power, a Y-intercept of the regression line, a slope of the regression line, mid-band fit, and an integrated backscatter parameter.

8. The system of claim 7, further comprising a signal conditioning element that adjusts the frequency domain representation of the RF signals according to an attenuation function.

9. The system of claim 8, wherein the signal conditioning element deconvolves the frequency domain representation of the RF signals to remove a transfer function of the ultrasound system.

10. The system of claim 7, wherein plurality of features includes at least one of a two-dimensional spectral feature and a feature based on a cepstrum determined from the set of harmonic data.

11. The system of claim 7, wherein the frequency range associated with second harmonics is the frequency range of the ultrasound system.

12. The system of claim 7, wherein one of the plurality of classes represent ablated tissue and one of the plurality of classes represent tissue that has not been ablated.

13. A method for use in an ultrasound system comprising:
receiving recorded echoes from a region of interest as a set of radio frequency (RF) signals;
transforming the RF signals from a time domain representation to a frequency domain representation;
adjusting the frequency domain representation for attenuation as a function of the depth of the region of interest;
extracting a plurality of features from the frequency domain representation; and
assigning the region of interest to one of a plurality of classes representing anatomical feature according to the extracted plurality of features at a classifier model;
wherein the RF signals including a set of harmonic signals being extracted from a frequency range associated with second harmonics of the recorded echoes, and extracting a plurality of features from the frequency domain representation comprising extracting at least one feature representing the set of harmonic signals;
wherein the function of the depth of the region of interest is a first function, associated with a first frequency band, the method further comprising determining a second function associated with a second frequency band, such that adjusting the frequency domain representation for attenuation comprises adjusting the frequency domain representation for attenuation with the first function for signals within the first frequency band and using the second function for signals within the second frequency band.

14. The method of claim 13, wherein the extracted at least one feature includes at least one of a two-dimensional spectral feature and a feature based on a cepstrum determined from the set of harmonic data.

15. The method of claim 13, wherein the region of interest is in a first subject and adjusting the frequency domain representation for attenuation as the function of the depth of the region of interest comprises determining the function using measured backscatter from known tissue in a second subject.

16. The method of claim 13, wherein determining the function comprises determining a function of each of the depth of the region of interest and a ratio of a thickness of skin and fat to a thickness of muscle within the patient.

17. The method of claim 13, wherein adjusting the frequency domain representation for attenuation as the function of the depth of the region of interest comprises determining the function using measured backscatter from known tissue in an ex vivo sample.

* * * * *